United States Patent [19]
Ciciarelli et al.

[11] Patent Number: 5,919,214
[45] Date of Patent: Jul. 6, 1999

[54] TWO-SIDED TELEMETRY IN IMPLANTABLE CARDIAC THERAPY DEVICES

[75] Inventors: Timothy E. Ciciarelli; Stephen T. Archer, both of Sunnyvale, Calif.

[73] Assignee: Pacesetter, Inc., Sunnyvale, Calif.

[21] Appl. No.: 08/967,872

[22] Filed: Nov. 12, 1997

[51] Int. Cl.$^6$ .................................................. A61N 1/362
[52] U.S. Cl. ................................ 607/32; 607/60; 128/903
[58] Field of Search ................................ 607/31, 32, 60; 128/903

[56] References Cited

U.S. PATENT DOCUMENTS

| | | | |
|---|---|---|---|
| 4,441,498 | 4/1984 | Nordling | 607/32 |
| 4,573,475 | 3/1986 | Dukes et al. | 128/903 |
| 4,809,697 | 3/1989 | Causey, III et al. | |
| 4,944,299 | 7/1990 | Silvian | |

*Primary Examiner*—William E. Kamm
*Assistant Examiner*—George R. Evanisko
*Attorney, Agent, or Firm*—Steven M. Mitchell

[57] ABSTRACT

A method for ensuring two-sided telemetry in implantable cardiac therapy devices by making at least one of the following operating parameters selectable (reversible): (1) the direction of current detection of the telemetry circuitry of the implantable cardiac therapy device; (2) the direction of the magnetic field produced by the transmit coil of an external telemetry device (programming wand); (3) the direction of the magnetic field produced by the T/R coil of the implantable cardiac therapy device; and/or (4) the direction of current detection of the telemetry circuitry of the programming wand. In a presently contemplated implementation, when it is desired to read-out data from the implantable cardiac therapy device and/or to re-program the device parameters, a telemetry operation is attempted in the normal manner, i.e., it is initiated by the programming wand. If the communication is unsuccessful, then the direction of the magnetic field produced by the transmit coil of the programming wand is reversed, and the telemetry operation repeated. If the transmission of command data from the programming wand to the implantable cardiac therapy device is successful, but the transmission of read-out data from the device to the programming wand is unsuccessful, then the direction of current detection of the telemetry circuitry of the programming wand is reversed, and the telemetry operation is attempted again; alternatively, the direction of the magnetic field produced by the T/R coil of the implantable cardiac therapy device can be reversed. Thus, no matter what the orientation of the device and external telemetry device, successful two-way telemetry between the device and the programming wand is possible. Thus, the telemetry can be considered "two-sided". In an alternative embodiment, the telemetry operation can be initiated by the implantable cardiac therapy device. In this case, if the communication is unsuccessful, then the direction of the magnetic field produced by the T/R coil of the device is reversed.

12 Claims, 6 Drawing Sheets

TWO-SIDED TELEMETRY IN IMPLANTABLE CARDIAC THERAPY DEVICES

BACKGROUND OF THE INVENTION

The present invention relates generally to implantable cardiac therapy devices, and more particularly, to a method and system for facilitating two-sided telemetry in implantable cardiac therapy devices.

Implantable cardiac therapy devices include implantable pacemakers and implantable cardioverter-defibrillators. An implantable pacemaker monitors the intrinsic electrical activity of the patient's heart and if a natural heart beat is not detected within a prescribed time period, the pacemaker delivers (via a lead system) an electrical stimulation or pacing pulse to force the heart muscle tissue to contract, thereby assuring that a minimum heart rate is maintained. In this way, bradycardia is terminated or prevented. Contemporary implantable cardioverter-defibrillators (ICDs) monitor the intrinsic electrical activity of the patient's heart in accordance with a diagnostic or detection algorithm by analyzing electrograms (EGMs) generated by sensing electrodes positioned proximate the sino-atrial and/or atrioventricular node of the patient's heart, and most advantageously, in the right ventricular apex of the patient's heart.

Typical current-generation ICDs are capable of delivering various types or levels of cardiac therapy (i.e., "tiered therapy"). The first type or level of therapy is bradycardia and antitachycardia pacing (ATP), in which a low level of electrical energy (generally between millionths to thousandths of a joule) is delivered to the patient's heart (via a lead system) in order to correct detected episodes of bradycardia or tachycardia, respectively. The second type or level of therapy is cardioversion, in which an intermediate level of electrical energy (generally between 1–5 joules) is delivered to the patient's heart (via a lead system) to terminate a detected episode of ventricular arrhythmia (e.g., a detected heart beat in the range of 130–190 beats/minute) or an ongoing episode of tachycardia that ATP therapy has failed to terminate. The third type or level of therapy is defibrillation, in which a high level of electrical energy (generally above 15 joules) is delivered to the patient's heart (via a lead system) in order to terminate a detected episode of ventricular fibrillation or an episode of ventricular tachycardia which has degraded into ventricular fibrillation due to failure of cardioversion therapy. The defibrillation energy is typically stored in a defibrillation energy storage capacitor ("output capacitor") which is charged by a high-voltage charging circuit, and then delivered as an electrical shock(s) by means of a high-voltage output switching circuit which discharges the output capacitor.

Current generation ICDs are microprocessor-controlled. The detection and diagnosis of cardiac arrhythmias which require treatment are performed in accordance with a complex detection or diagnostic algorithm programmed into the microprocessor, and the delivery of the appropriate form of cardiac therapy is controlled in accordance with an equally complex therapy delivery algorithm programmed into the microprocessor. The goal is to optimize the therapy for a given patient using the lowest amount of energy which is possible (for a given safety margin), thereby enabling the ICD to be made as small as possible.

Current generation ICDs store electrogram, device operating status (e.g., battery status and lead impedance), and diagnostic data in device memory (e.g., RAM). An external data telemetry device (sometimes referred to as a "programming wand") is employed by the patient's physician to telemetrically read-out the stored data in a non-invasive manner, with little or no discomfort to the patient. The patient's physician can analyze the telemetered data in order to evaluate the status of the device and the therapeutic efficacy thereof. The telemetered data can aid the physician in gaining a better understanding of the etiology of the patient's underlying cardiac condition, and enable the physician to better "customize" the therapy administered by the ICD for the patient by telemetrically reprogramming the device using the programming wand.

As can be appreciated from the foregoing, the capability of telemetrically interrogating and programming the ICD using an external, programming wand is of critical importance. Generally, the programming wand-ICD telemetry interface includes separate transmit and receive coils in the programming wand and a single transmit/receive (T/R) coil in the ICD. A typical programming wand is disclosed in U.S. Pat. No. 4,809,697 and typical telemetry circuitry is disclosed in U.S. Pat. No. 4,944,299, the disclosures of which are incorporated herein by reference.

Data (such as device status, diagnostic, and electrogram data) is telemetrically read-out of the ICD by flowing a current through the T/R coil in a fixed direction, thereby producing a magnetic field having a fixed direction. The magnetic field produced by the current flowing through the T/R coil of the ICD induces a corresponding current in the receive coil of the external programming wand, when the programming wand is held in close proximity to the patient's chest at the location where the ICD is implanted. The current is RF-modulated in accordance with the data being transmitted. Thus, the RF-modulated current constitutes an information signal which can be converted by an A/D converter in the programming wand and then decoded by suitable decoding circuitry in a customized desktop or laptop personal computer to which the programming wand is coupled, to thereby reconstitute the original data for presentation to the physician (typically on a display screen of the customized personal computer).

Data (such as command data for re-programming the ICD) is telemetrically programmed into the ICD by RF-modulating current flowing through the transmit coil of the programming wand in a fixed direction, thereby producing a magnetic field having a fixed direction. The magnetic field produced by the current flowing through the transmit coil of the programming wand induces a corresponding current in the T/R coil of the ICD, when the programming wand is held in close proximity to the patient's chest at the location where the ICD is implanted. Again, the current is RF-modulated in accordance with the data being transmitted. Thus, the current constitutes an information signal which can be converted by an A/D converter in the ICD and then decoded by suitable decoding circuitry in the ICD, to thereby reconstitute the original data for processing by the microprocessor and/or other appropriate logic hardware within the ICD.

Although the above-described ICD-programming wand telemetry interface has proven quite adequate for most situations, it does suffer from at least the following significant shortcoming. Namely, successful telemetry using the presently available programming wands requires a "correct" orientation of the programming wand and ICD. The "correct" orientation is the orientation in which the fixed direction of the magnetic field produced by the programming wand induces current flow through the T/R coil of the ICD in the fixed direction for which the telemetry circuitry in the ICD is designed to detect current flow through the T/R coil.

The "correct" orientation is depicted in FIG. 1. However, if the ICD is flipped so that the device and the programming wand are not in the "correct" orientation, telecommunication (telemetry) between the programming wand and the ICD is not possible. This situation is depicted in FIG. 2. In this connection, an ICD can be inadvertently flipped as a result of a patient's twiddling with the device by manipulating the skin of his or her chest where the device is implanted, a condition which has been dubbed "twiddler's syndrome".

Another shortcoming of the existing programming wand-ICD telemetry interface is that the device must be implanted with the "correct" side up in order to facilitate "correct" orientation of the programming wand and the device. Thus, the leads that are connected to the device must trail out of one side of the device, e.g., the right side, even though it may be desired that the leads trail out of the other side of the device, e.g., the left side. In short, the requirement of a single "correct" orientation (or, "one-sidedeness" of the wand-ICD telemetry interface) acts as a constraint on the implantation of the device.

Based on the above and foregoing, it can be appreciated that there presently exists a need in the art for a programming wand-ICD telemetry interface which overcomes the above-described shortcomings of the presently available technology. The present invention fulfills this need in the art.

SUMMARY OF THE INVENTION

The present invention encompasses a method for ensuring two-sided telemetry in implantable cardiac therapy devices by making at least one of the following operating parameters of the system selectable (reversible): (1) the direction of current detection of the telemetry circuitry of the implantable cardiac therapy device; (2) the direction of the magnetic field produced by the transmit coil of the external telemetry device; (3) the direction of the magnetic field produced by the T/R coil of the implantable cardiac therapy device; and/or (4) the direction of current detection of the telemetry circuitry of the external telemetry device (e.g., programming wand).

In a presently preferred embodiment, when it is desired to read-out data from the implantable cardiac therapy device and/or to re-program the device parameters, a telemetry operation is attempted in the normal manner, i.e., it is initiated by the programming wand. If the communication is unsuccessful, then the direction of the magnetic field produced by the transmit coil of the programming wand is reversed, and the telemetry operation repeated. If the transmission of command data from the programming wand to the implantable cardiac therapy device is successful, but the transmission of read-out data from the device to the programming wand is unsuccessful, then the direction of current detection of the telemetry circuitry of the programming wand is reversed, and the telemetry operation is attempted again; alternatively, the direction of the magnetic field produced by the T/R coil of the implantable cardiac therapy device can be reversed. Thus, no matter what the orientation of the device and external telemetry device, successful two-way telemetry between the device and the programming wand is possible. Thus, the telemetry can be considered "two-sided".

In an alternative embodiment, the telemetry operation can be initiated by the implantable cardiac therapy device. In this case, if the communication is unsuccessful, then the direction of the magnetic field produced by the T/R coil of the device is reversed.

The sequences of the above-described preferred and alternative embodiments can be considered to constitute a "hand-shaking routine" which is executed when a telemetry operation is attempted.

BRIEF DESCRIPTION OF THE DRAWINGS

These and various other features and advantages of the present invention will be readily understood with reference to the following detailed description taken in conjunction with the accompanying drawings, in which.

DETAILED DESCRIPTION OF THE INVENTION

In overview, the present invention overcomes the limitations of the existing technology relating to the implantable cardiac therapy device-external telemetry device system by making at least one of the following operating parameters of the system selectable (reversible):

(1) the direction of current detection of the telemetry circuitry of the implantable cardiac therapy device;

(2) the direction of the magnetic field produced by the transmit coil of the external telemetry device;

(3) the direction of the magnetic field produced by the T/R coil of the implantable cardiac therapy device;

(4) the direction of current detection of the telemetry circuitry of the programming wand.

The manner in which the selectability (reversibility) of at least one of the above-enumerated parameters is implemented is not limiting to the present invention, in its broadest sense. In a presently contemplated implementation, when it is desired to read-out data from the implantable cardiac therapy device (hereinafter "device) and/or to re-program the device parameters, a telemetry operation is attempted in the normal manner, i.e., it is initiated by the external telemetry device (hereinafter "programming wand"). If the communication is unsuccessful, then the direction of the magnetic field produced by the transmit coil of the programming wand is reversed, and the telemetry operation repeated. If the transmission of command data from the programming wand to the implantable cardiac therapy device is successful, but the transmission of read-out data from the device to the programming wand is unsuccessful, then the direction of current detection of the telemetry circuitry of the programming wand is reversed, and the telemetry operation is attempted again; alternatively, the direction of the magnetic field produced by the T/R coil of the implantable cardiac therapy device can be reversed, (e.g., via appropriate commands issued by the programming wand). Thus, no matter what the orientation of the device and programming wand, successful two-way telemetry between the device and the programming wand is possible. In this regard, the telemetry can be considered "two-sided". The sequence described above can be considered to constitute a "handshaking routine" which is executed when any telemetry session is initiated.

Figure 1:
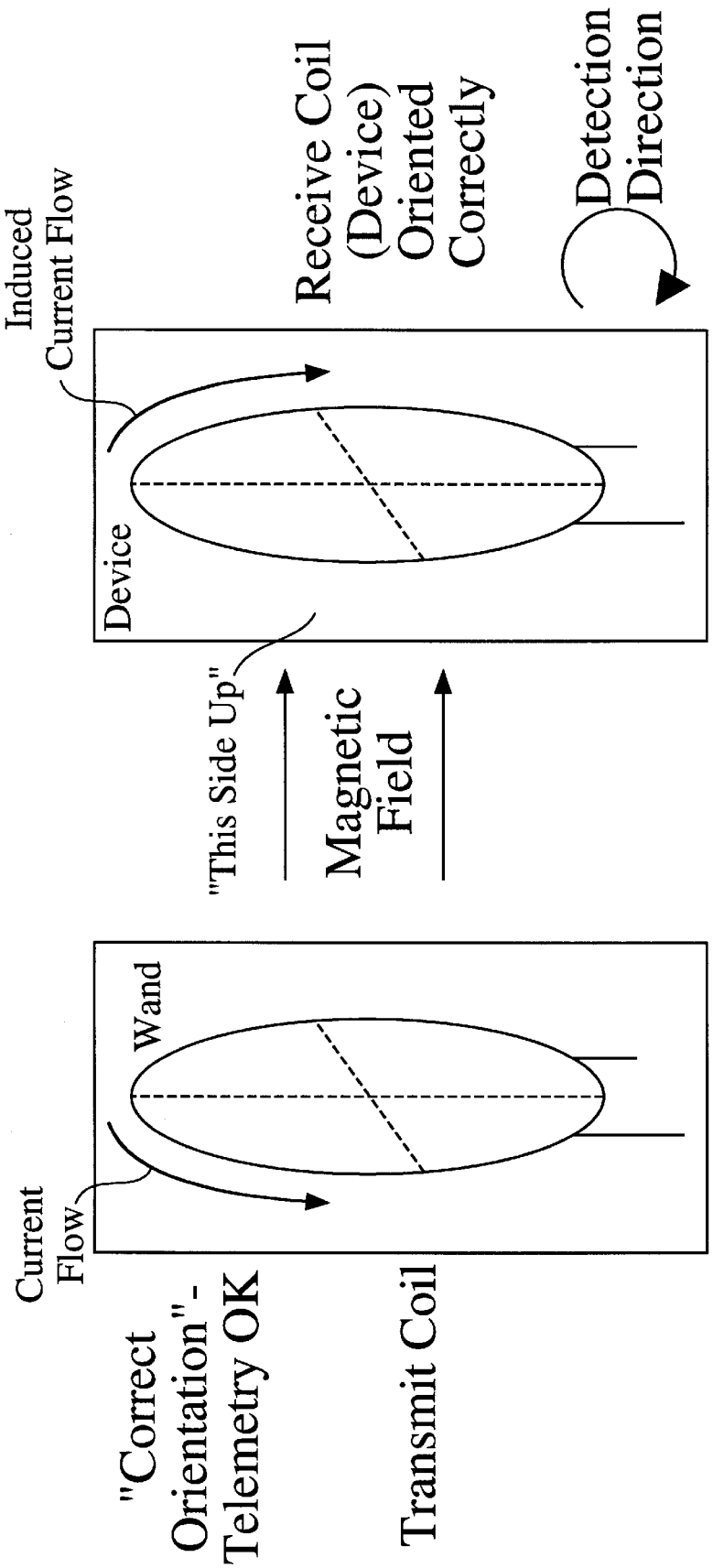
FIG. 1 is a diagrammatical depiction of the "correct" orientation of an implantable cardiac therapy device and programming wand.
Figure 2:
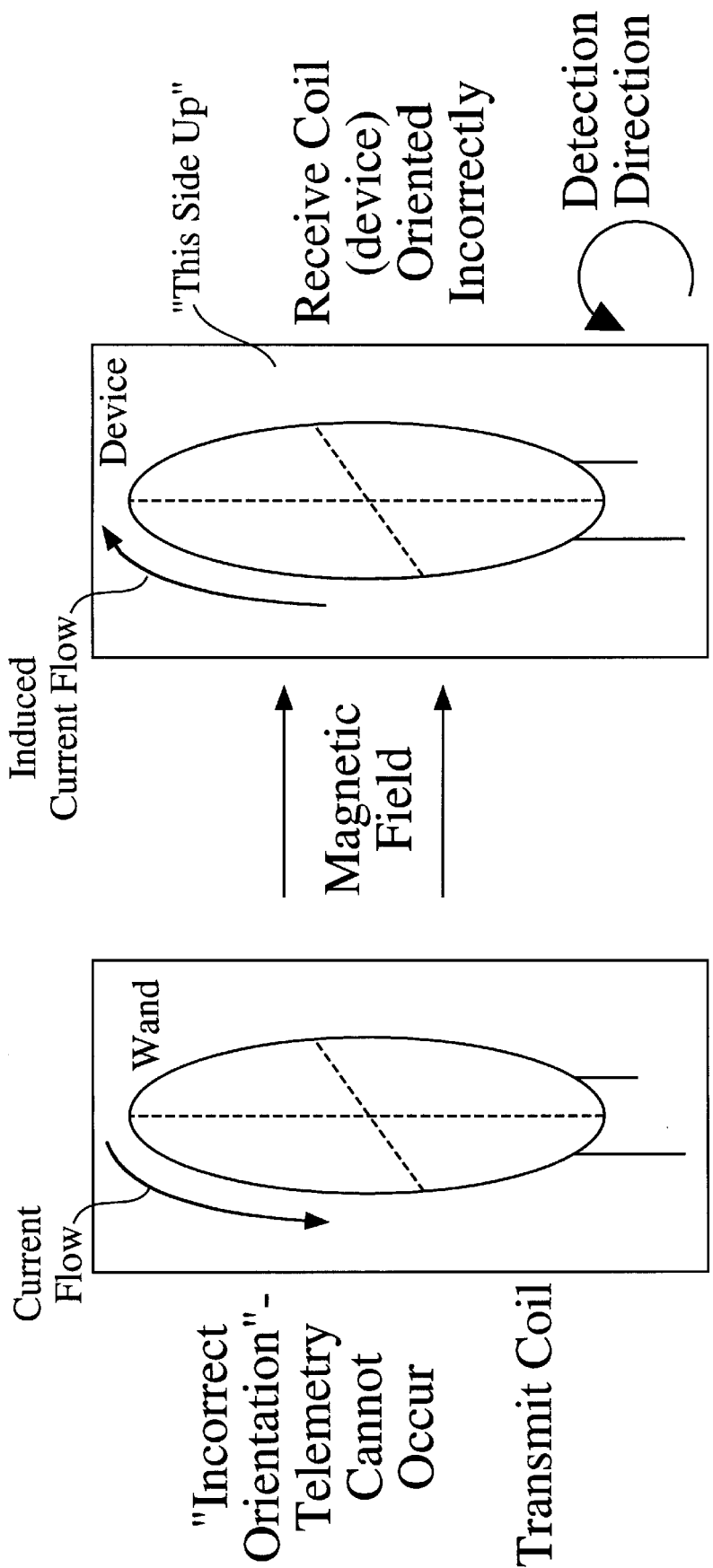
FIG. 2 is a diagrammatical depiction of the "incorrect" orientation of an implantable cardiac therapy device and programming wand.
Figure 3:
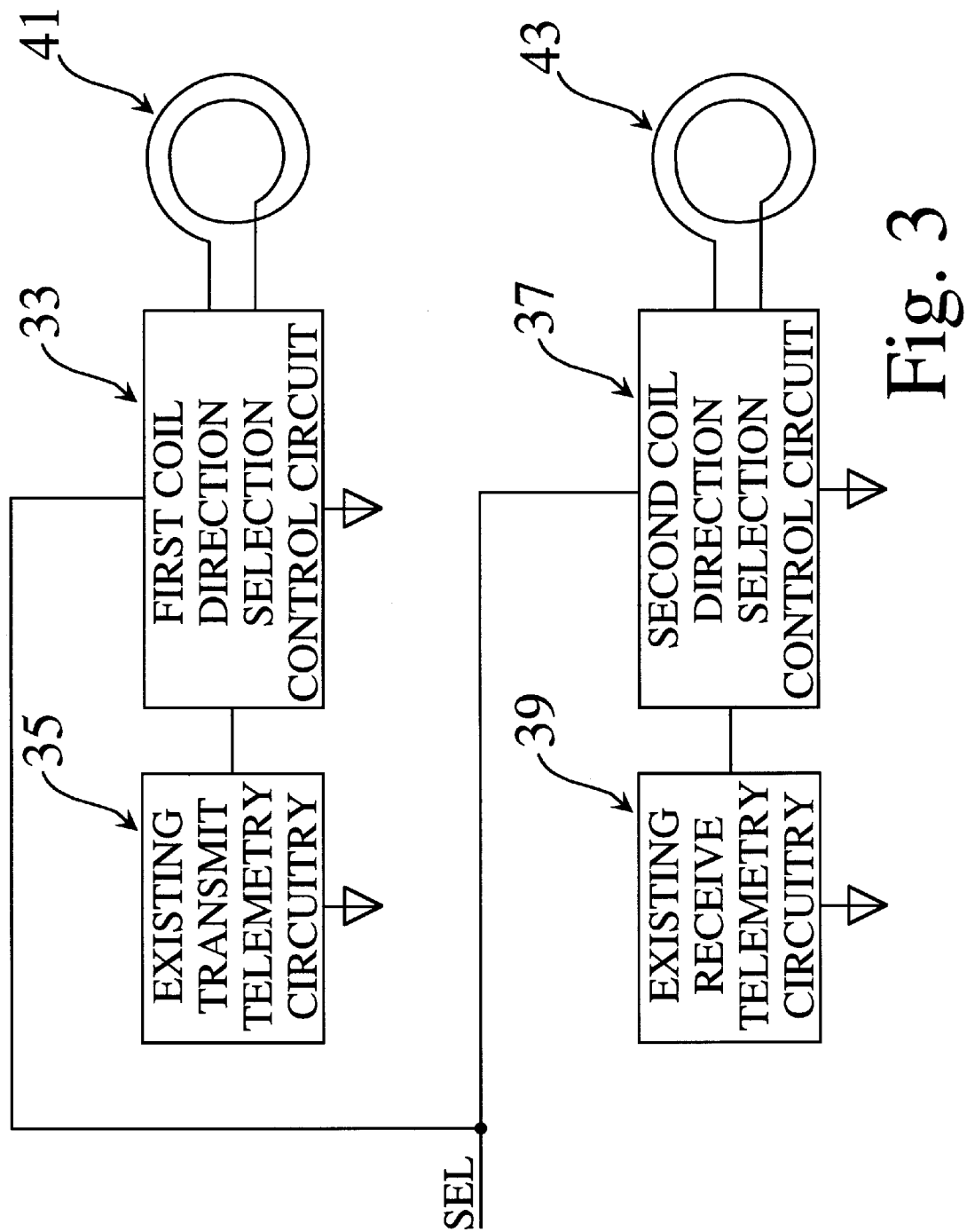
FIG. 3 is a block diagram of an exemplary implementation of a preferred embodiment of the present invention.

With reference now to FIG. 3, there can be seen a block diagram of an exemplary implementation of the preferred embodiment of the present invention, in which a first coil direction selection circuit 33 is inserted between the transmit coil 41 and the existing transmit telemetry circuitry 35 in the programming wand, and a second coil direction selection circuit 37 is inserted between the receive coil 43 and the existing receive telemetry circuitry 39 in the programming wand. Each of the coil direction selection circuits 33 and 37 is controlled by the same control signal "SED" and can suitably be of the same design as the selection control circuit 20 depicted in FIG. 4 (and described in detail below). By utilizing separate coil direction selection circuits for the transmit and receive coils 41, 43, respectively, the direction of current detection by the receive telemetry circuitry 39 with respect to current induced in the receive coil 43 by a magnetic field produced by the T/R coil of the implantable cardiac therapy device (i.e., the direction in which the receive coil 43 is "listening") will be the same as the direction in which current flows through the transmit coil 41 of the wand (i.e., the direction in which the transmit coil 41 is transmitting).

Figure 4:
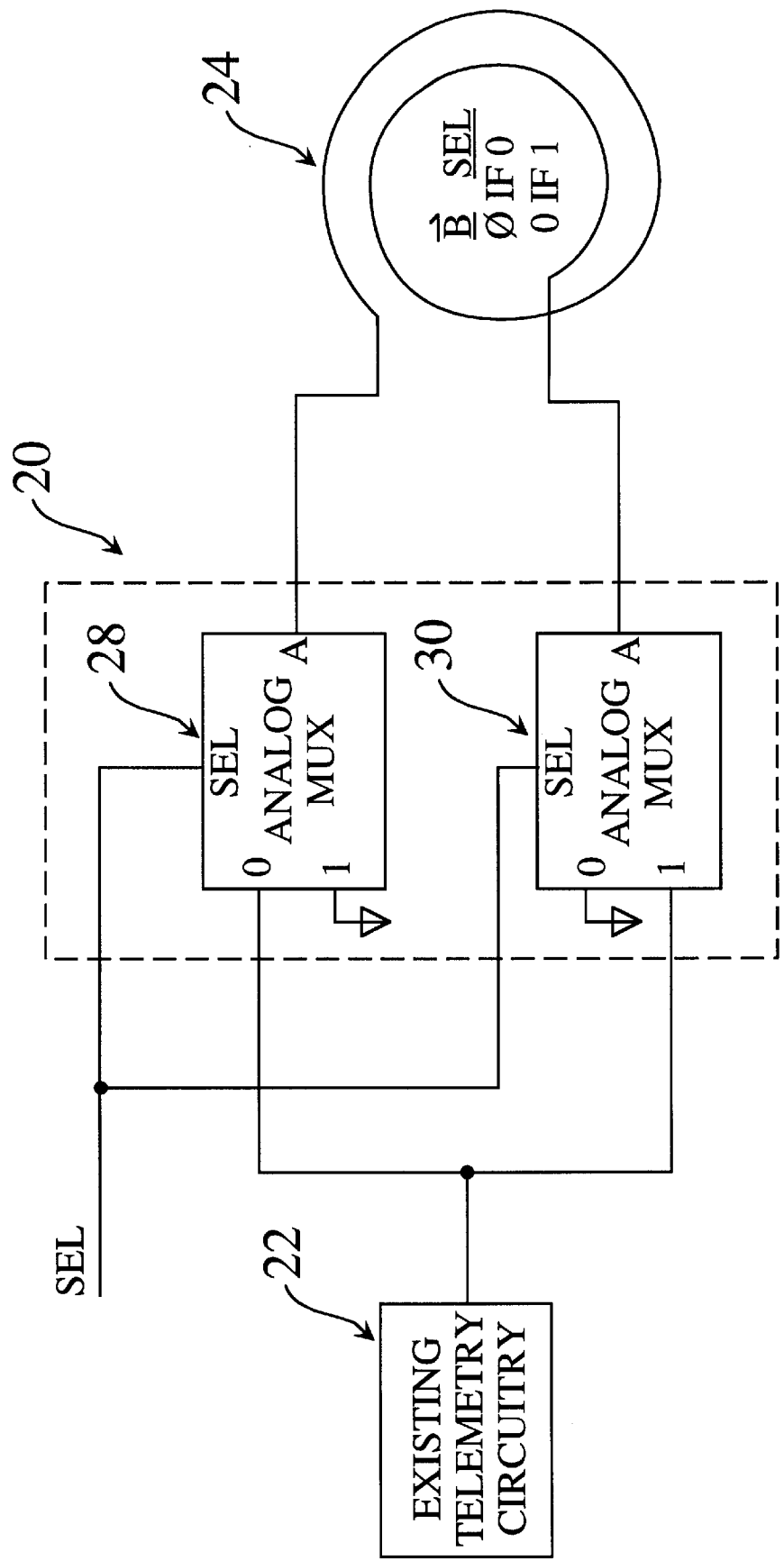
FIG. 4 is a block diagram of a first exemplary implementation of an alternative embodiment of the present invention.

With reference now to FIG. 4, there can be seen a block diagram of a first exemplary implementation of an alternative embodiment of the present invention, which can be employed when it is desired to provide the capability of the implantable cardiac therapy device to initiate telemetry operations. In accordance with this first exemplary implementation of the alternative embodiment of the present invention, a "new" (additional) circuit 20 (hereinafter "selection control circuit") is inserted between the existing telemetry circuitry 22 and the T/R coil of the implantable cardiac therapy device. The function of the existing telemetry circuitry 22 remains the same, i.e., to generate pulses which cause current to flow through the T/R coil 24 during a transmit mode of operation, and to detect current induced through the T/R coil 24 by the magnetic field produced by the programming wand during a receive mode of operation. The function of the selection control circuit 20 is to selectively control the direction in which the current flows through the T/R coil 24 in response to the pulses generated by the telemetry circuitry 20, and thereby selectively control the direction of the magnetic field produced by the current flowing through the T/R coil 24.

In particular, the selection control circuit 20 includes a first analog multiplexer 28 and a second analog multiplexer 30 each of which have a select input "SEL" and two data inputs "0" and "1". The output of the telemetry circuitry 20 is applied to the "0" input of the multiplexer 28 and to the "1" input of the multiplexer 30. The "1" input of the multiplexer 28 and the "0" input of the multiplexer 30 are connected to ground (or Vss). The select input "SEL" constitutes a control signal which can be generated by the microprocessor or other logic hardware in the implantable cardiac therapy device, e.g., upon detecting that an initial telemetric communication attempt was unsuccessful. Depending upon the logic level of the control signal "SEL", the pulse generated by the telemetry circuitry 20 will be transmitted through either the multiplexer 28 or 30, so that the direction of current flow through the T/R coil 24 (and thus, the direction of the magnetic field produced thereby) is selectable. It will be appreciated that as long as the multiplexers 28 and 30 are bi-directional, this scheme will work for the wand transmit coil, the wand receive coil, and/or the device T/R coil.

Figure 5:
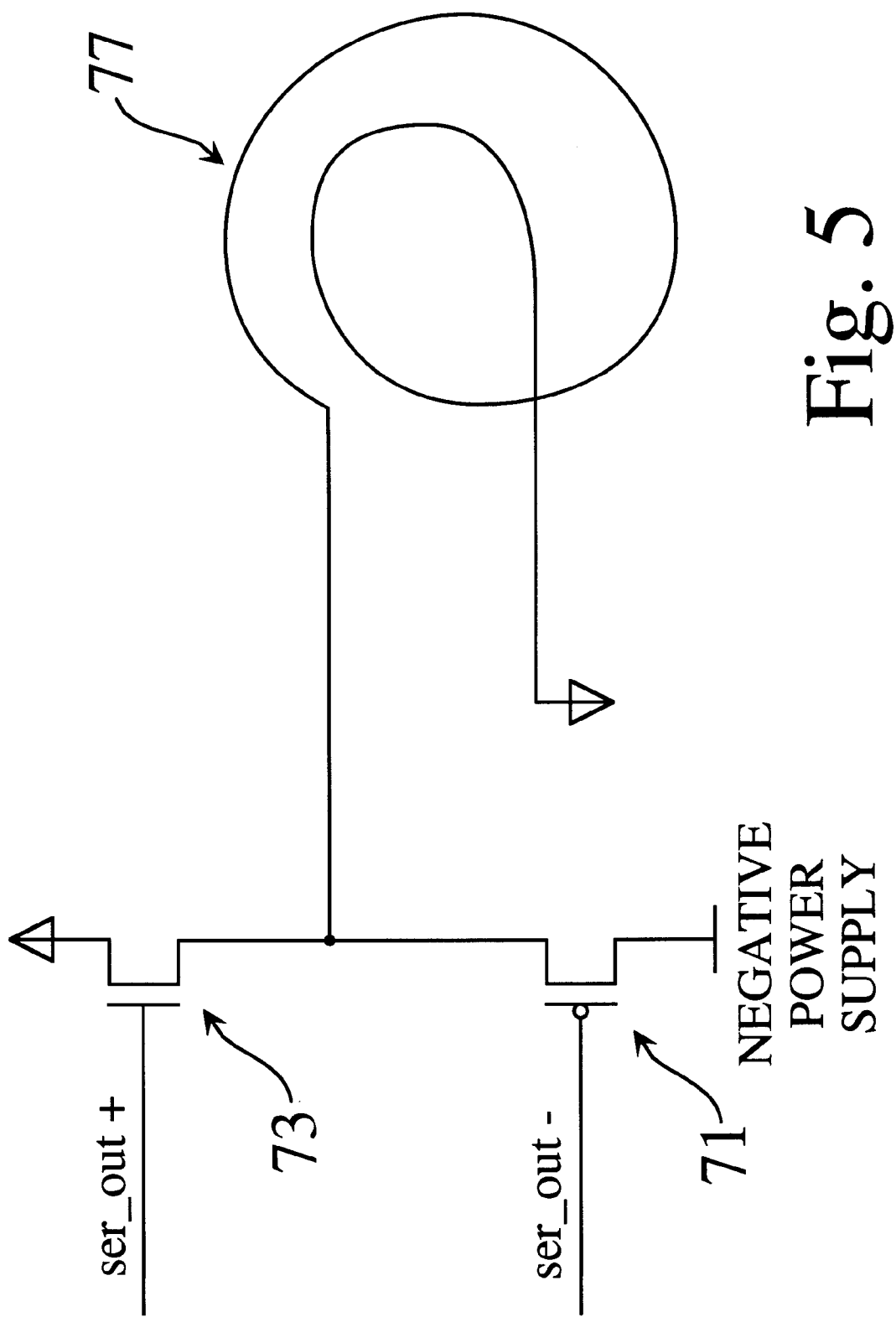
FIG. 5 is a schematic diagram of a second exemplary implementation of the alternative embodiment of the present invention; and, FIG. 6 is a schematic diagram of a third exemplary implementation of the alternative embodiment of the present invention.

With reference now to FIG. 5, there can be seen a second exemplary implementation of the alternative embodiment of the present invention in which the transmit direction of the implantable cardiac therapy device can be selected without the use of an analog multiplexer. More particularly, a PMOS transistor 71 is coupled between an NMOS transistor 73 (which is part of the existing transmit telemetry circuitry of the device) and a negative power supply. The "ser_out+" and "ser_out−" analog signals can be used to turn on either the PMOS transistor 71 or the NMOS transistor 73, to thereby selectively flow current in either direction through the T/R coil 77, and thereby selectively control the direction of the magnetic field induced thereby. Control logic from the device microprocessor could be utilized to control whether "ser_out+" or "ser_out−" is enabled.

Figure 6:
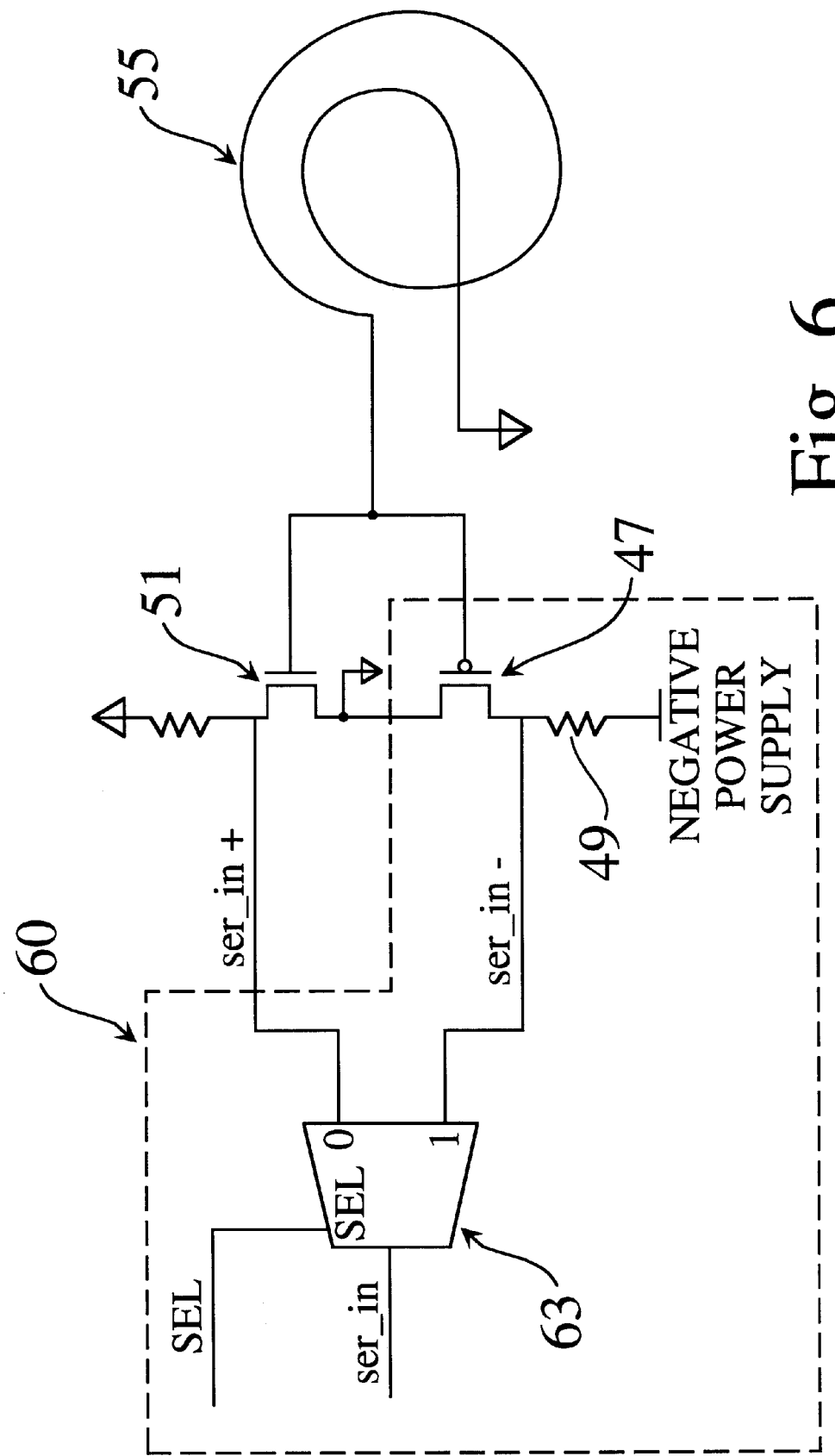

With reference now to FIG. 6, there can be seen a third exemplary implementation of the alternative embodiment of the present invention in which the receive direction of the implantable cardiac therapy device can be selected without the use of an analog mux. This implementation can be useful when the transmission of read-out data from the implantable cardiac therapy device to the programming wand is successful, but the receipt of command data from the programming wand is unsuccessful (and, for example, the programming wand does not have the capability of reversing the direction of its transmit coil). More particularly, a PMOS transistor 47 and resistor 49 are coupled between an NMOS transistor 51 and a negative power supply, with the gate of the PMOS transistor 47 being coupled to the gate of the NMOS transistor 51, and both gates being commonly coupled to a first end of the T/R coil 55. The circuitry contained within the dotted outline labeled 60 constitutes the receive direction selection control circuitry. The circuitry outside of the dotted outline 60 constitutes the existing receive telemetry circuitry of the device. The receive direction selection control circuitry further includes a digital multiplexer 63 having a select input "Sel", an analog signal input "ser_in", and decoded outputs "0" ("ser_in+") and "1" ("ser_in−"). The control signal "SEL" is used to select either the decoded output "ser_in+" or "ser_in−", and thereby control the direction of current detection with respect to the current flowing through the T/R coil 55.

Although a several exemplary implementations of various preferred and alternative embodiments of the present invention have been described in detail hereinabove, it should be clearly understood that many other variations and/or modifications of the basic inventive concepts herein taught which may appear to those skilled in the pertinent art will still fall within the spirit and scope of the present invention, as defined in the appended claims.

What is claimed is:

1. A method for telemetrically communicating with an implantable medical device having a receive coil and first telemetry circuitry, using an external telemetry device having a transmit coil and second telemetry circuitry, the method comprising the steps of:

flowing current in a first current direction through the transmit coil of the telemetry device, to thereby produce a magnetic field having a first field direction;

holding the telemetry device in proximity to the implantable medical device, whereby a current which flows in the first current direction is induced in the receive coil of the implantable medical device to communicate with the implantable medical device;

determining whether communication has been successfull or unsuccessful; and, if it is determined in the determining step that communication has been unsuccessful, then flowing the current in a second current direction through the transmit coil of the telemetry device, to thereby produce a magnetic field having a second field direction, whereby a current which flows in the second current direction is induced in the receive coil of the implantable medical device.

2. The method as set forth in claim 1, wherein the implantable medical device comprises an implantable cardiac therapy device.

3. The method as set forth in claim 1, wherein the telemetry device comprises a programming wand.

4. A telemetry system for telemetrically communicating with an implantable medical device, comprising:

a communication coil;

means for selectively flowing a current pulse in either a first direction or a second direction through the communication coil, to thereby produce a selectively reversible magnetic field pulse and to provide telemetric communication;

means for detecting whether the telemetric communication was successful; and means for flowing the current pulse in an opposite direction if the telemetric communication was unsuccessful.

5. The telemetry system as set forth in claim 4, wherein the communication coil comprises a transmit coil.

6. A system, comprising:

an implantable medical device having a receive coil and first telemetry circuitry;

an external telemetry device having a transmit coil and second telemetry circuitry for transmitting a signal from the transmit coil of the external telemetry device to the receive coil of the implantable medical device to thereby provide telemetric communication between the implantable medical device and the external telemetry device;

means for flowing current in a first direction through the transmit coil of the external telemetry device;

means for detecting whether a telemetric communication between the external telemetry device and the implantable medical device has been successful or not: and, means responsive to detection of an unsuccessful telemetric communication for reversing the direction of current flow through the transmit coil of the external telemetry device.

7. A system, comprising:

an external telemetry device for providing telemetric communication with an implantable medical device the external telemetry device having a receive coil;

an implantable medical device having a transmit coil;

means for flowing current in a first direction through the transmit coil of the implantable medical device to provide telemetric communication with the external telemetry device;

means for detecting whether a telemetric communication has been successful or not; and, means responsive to detection of an unsuccessful telemetric communication for reversing the direction of current flow through the transmit coil of the implantable medical device.

8. A method for telemetrically reading out data from an implantable medical device having a transmit coil and first telemetry circuitry, using an external telemetry device having a receive coil and second telemetry circuitry, the method comprising the steps of:

flowing current in a first current direction through the transmit coil of the implantable medical device, to thereby produce a magnetic field having a first field direction;

holding the telemetry device in proximity to the implantable medical device, whereby a current which flows in the first direction is induced in the receive coil of the telemetry device;

determining whether a read-out has been successful or unsuccessful; and, if it is determined that the read-out has been unsuccessful, then flowing the current in a second current direction through the transmit coil of the implantable medical device, to thereby produce a magnetic field having a second field direction, whereby a current which flows in the second current direction is induced in the receive coil of the telemetry device.

9. A method for telemetrically reading out data from an implantable medical device having a transmit coil and first telemetry circuitry, using an external telemetry device having a receive coil and second telemetry circuitry, the method comprising the steps of:

flowing current in a first current direction through the transmit coil of the implantable medical device, to thereby produce a magnetic field having a first field direction;

holding the telemetry device in proximity to the implantable medical device, whereby a current which flows in the first current direction is induced in the receive coil of the telemetry device;

determining whether the read-out has been successful or unsuccessful; and, if it is determined in the determining step that the read-out has been unsuccessful, then reversing the direction of current flow of the second telemetry circuitry of the telemetry device.

10. A method for telemetrically communicating with an implantable medical device having a receive coil and first telemetry circuitry, using an external telemetry device having a transmit coil and second telemetry circuitry, the method comprising the steps of:

flowing current in a first current direction through the transmit coil of the telemetry device, to thereby produce a magnetic field having a first field direction;

holding the telemetry device in proximity to the implantable medical device, whereby a current which flows in the first current direction is induced in the receive coil of the implantable medical device;

determining whether or not the second telemetry circuitry has detected a signal in the receive coil; and, if it is determined that the second telemetry circuitry has not detected a signal in the receive coil, then reversing the direction of current flow in the transmit coil.

11. The method as set forth in claim 10, wherein the implantable medical device comprises an implantable cardiac therapy device.

12. The method as set forth in claim 10, wherein the telemetry device comprises a programming wand.

* * * * *